United States Patent
Doguet et al.

(10) Patent No.: US 11,975,207 B2
(45) Date of Patent: May 7, 2024

(54) ACTIVE IMPLANTABLE MEDICAL DEVICE INCLUDING AN OPTICAL ACTION TRIGGER

(71) Applicant: Synergia Medical, Mont-Saint-Guibert (BE)

(72) Inventors: Pascal Doguet, Mont-Saint-Guibert (BE); Yoan Botquin, Mont-Saint-Guibert (BE); Jérôme Garnier, Mont-Saint-Guibert (BE)

(73) Assignee: Synergia Medical, Mont-Saint-Guibert (BE)

( * ) Notice: Subject to any disclaimer, the term of this patent is extended or adjusted under 35 U.S.C. 154(b) by 0 days.

(21) Appl. No.: 18/035,577

(22) PCT Filed: Nov. 10, 2020

(86) PCT No.: PCT/EP2020/081568
§ 371 (c)(1),
(2) Date: May 5, 2023

(87) PCT Pub. No.: WO2022/100811
PCT Pub. Date: May 19, 2022

(65) Prior Publication Data
US 2023/0302286 A1    Sep. 28, 2023

(51) Int. Cl.
*A61N 1/378* (2006.01)
*A61N 1/36* (2006.01)

(52) U.S. Cl.
CPC ....... *A61N 1/3787* (2013.01); *A61N 1/36053* (2013.01); *A61N 1/36125* (2013.01)

(58) Field of Classification Search
CPC .. A61N 1/36; A61N 1/36052; A61N 1/36125; A61N 1/3787
See application file for complete search history.

(56) References Cited

U.S. PATENT DOCUMENTS

| | | | | |
|---|---|---|---|---|
| 7,435,229 B2 * | 10/2008 | Wolf | ............... | A61B 5/031 600/561 |
| 8,527,046 B2 * | 9/2013 | Connelly | ............ | A61N 1/37512 607/9 |

(Continued)

OTHER PUBLICATIONS

Int'l Search Report for PCT/EP2020/081568, dated Jul. 14, 2021.

*Primary Examiner* — Christopher A Flory
(74) *Attorney, Agent, or Firm* — MaxGoLaw PLLC

(57) ABSTRACT

A kit-of-parts for initiating an action by an active implantable medical device (AIMD) (1) implanted in a body of a patient triggered by an external triggering unit (11) located outside the body of the patient is provided. The kit-of-parts including,
(A) the external triggering unit (11) including an external emitter (12) which includes one or more sources of light (12L) configured for emitting an optical starting signal (10), and
(B) the AIMD (1) including an encapsulation unit (1e) defining an inner volume containing an action trigger configured for initiating an action by the AIMD (1), upon reception of the optical starting signal (10) from the external triggering unit (11). The action trigger is an optical action trigger (2) includes one or more photodetectors (2*pv*) facing a transparent wall portion (1*t*) and configured for transforming the optical starting signal (10) into an electrical signal to initiate the action by the AIMD.

14 Claims, 3 Drawing Sheets

(56) References Cited

U.S. PATENT DOCUMENTS

| | | | |
|---|---|---|---|
| 2003/0036776 A1* | 2/2003 | Foster | A61N 1/37512 607/9 |
| 2008/0071328 A1* | 3/2008 | Haubrich | A61N 1/37276 607/60 |
| 2009/0132018 A1* | 5/2009 | DiUbaldi | A61N 1/0492 607/152 |
| 2015/0077050 A1* | 3/2015 | Van Funderburk | A61N 1/3787 320/108 |
| 2015/0080982 A1 | 3/2015 | Van Funderburk | |
| 2016/0287885 A1 | 10/2016 | Saini | |
| 2016/0303384 A1* | 10/2016 | Sahin | A61N 5/0622 |
| 2017/0049336 A1* | 2/2017 | Hatch | A61B 5/02427 |
| 2017/0316487 A1* | 11/2017 | Mazed | G06Q 30/0241 |
| 2017/0368358 A1* | 12/2017 | Doguet | A61N 1/3787 |
| 2018/0109946 A1 | 4/2018 | Mosenia et al. | |
| 2019/0168004 A1* | 6/2019 | Doguet | A61N 1/37223 |
| 2019/0168022 A1* | 6/2019 | Doguet | G02B 6/4228 |
| 2021/0106833 A1* | 4/2021 | von Arx | A61N 1/37288 |

* cited by examiner

ACTIVE IMPLANTABLE MEDICAL DEVICE INCLUDING AN OPTICAL ACTION TRIGGER

TECHNICAL FIELD

The present invention concerns an active implantable medical device (AIMD) configured for being implanted in a body of a patient. The AIMD of the present invention is provided with an optical action trigger, configured for detecting an optical starting signal from an external triggering unit without consuming any energy from the battery enclosed in the AIMD. The AIMD comprises an implanted control logic configured for analysing the optical starting signal and deciding whether or not to initiate one or more predefined actions by the AIMD. In case the AIMD is a neurostimulator comprising an implanted pulse generator (IPG), the predefined actions can comprise modifying one or more parameters of the pulses generated by the IPG. The predefined action can include initiating a communication between the AIMD and an external communication unit or measuring a physiological sign of the patient. Doing so, the AIMD of the present invention is protected against remote hacking using RF-communication waves (e.g., WIFI, Bluetooth), as a communication, even by RF, can only be initiated by an communication between the external triggering unit and the optical action trigger, which can only function at very close range (of the order of cm). Any other predefined action can be set such as initiating some sensing, launching specific software routine or modifying any types of parameters.

BACKGROUND OF THE INVENTION

Active implantable medical devices (AIMD) have been used for decades for treating a number of disorders, in particular neurological disorders. Active implantable medical devices (AIMD) distinguish from (non-active) implantable medical devices (IMD), like RFID tags and the like, in that AIMD's are configured for actively interacting with the body they are implanted in, such as by stimulating tissues, monitoring vital signs, and the like. Generally, AIMD's are able to transfer energy from and to the implant. AIMD's therefore generally enclose a source of energy, such as a battery or a rechargeable battery.

A major type of AIMD's consists of neurostimulators, which deliver electrical pulses to a tissue such as a nerve (e.g., vagus nerve) or a muscle for diagnosing or treating a number of disorders such as Parkinson's disease, epilepsy, chronic pain, motor disorders, and many other applications. Depending on the tissue to be treated, the type of electrodes used, and the distance between electrodes, the voltage required between implanted electrodes is generally of the order of 15V±5V. Such voltage requires an electrical pulse generator of such dimensions that electric stimulating implants are generally formed of two separate components: on the one hand, the electrodes which are implanted directly onto the tissue to be treated and, on the other hand, the electrical pulse generator, of larger dimensions, and enclosed in an encapsulation, which can be implanted subcutaneously at various locations in the body depending upon the application. The encapsulation can be implanted in the subclavian region, the lower abdominal area or gluteal region, and the like. The encapsulation is generally made of titanium (alloys) for its mechanical properties and for other reasons, such as biocompatibility and easy processability. Encapsulations made of titanium have, however, low to no transmission to RF, visible and IR wavelengths, and are not MRI-friendly, generating heat and imaging artefacts. Some encapsulations have been made in ceramic materials, opaque or transparent to visible and IR lights. Polymers have been tested for encapsulations, but they generally lack durability and resistance to moisture.

As shown in FIG. 1($a$), in its simplest form, a device for delivering energy pulses comprises an implantable pulse generator (IPG) lodged in a housing of an encapsulation, a tissue coupling unit, and an energy transfer lead coupling the tissue coupling unit to the IPG to transmit energy from the IPG to the tissue coupling unit in the form of electrical or optical energy. The IPG can generate electrical pulses transmitted to the electrodes of the tissue coupling unit by conductive wires. Alternatively, and as described, e.g., in EP311383861, the IPG can generate light pulses transmitted through optical fibres either to an optrode, or to a photovoltaic cell which transforms the light energy into electrical energy which is fed to the electrodes. The term "energy transfer lead" is herein used to define both electric conductors (e.g., wires, tapes) and optical fibres.

Beside an IPG, neurostimulators generally comprise enclosed in the encapsulation thereof, a control logic, an implanted communication unit for communicating with an external communication unit, configured at least for receiving instructions but preferably for communicating both ways, and an implanted battery for powering the foregoing elements. The IPG is configured for delivering energy pulses according to one or more predefined programs saved in the control logic, or upon receiving instructions from the external communication unit overruling the predefined program currently running. Generally, albeit not necessarily, communication between the AIMD and the external unit proceeds using radio-frequency (RF) waves. In such configuration, the implanted communication unit is activated periodically to be ready to initiate a communication session upon receiving a corresponding starting signal from the external unit. This periodic activation, though moderately, is energy consuming. Since the sole source of energy available in the encapsulation is the battery, this operation reduces the service life of the battery or, for rechargeable batteries, it reduces the service time between two charging operations. Furthermore, it is an open door to malevolent hackers, who can send multiple RF-signals requiring communication power up and treatment in an attempt to hack into the system or to drain the battery power. In August 2017 the US Food and Drug Administration (FDA) recalled nearly 500,000 implantable pacemakers because of their potential vulnerability to hacking. Even in case of a safety feature, not allowing any action to be triggered, the whole validation and communication operation is energy consuming and such exercise rapidly leads to a swift discharge of the battery, which is even more critical if using a non-rechargeable unit.

It is a recurrent need to reduce energy consumption of AIMD's. In particular, reduction of energy consumption related to treatment of signals received from an external source is an on-going issue. For example, there is a special version of Bluetooth called Bluetooth Low Energy technology, which reduces considerably power consumption compared with the classical Bluetooth (=Bluetooth Basic Rate).

U.S. Pat. No. 5,154,172 describes an AIMD which changes the voltage applied to certain internal components during stimulation periods to allow full power operation during those intervals and reduced power levels at other intervals. The AIMD is reset by placing a magnet in a given location in conjunction with the application of a radio frequency transmission for a given period. The magnet is part of a trigger for triggering the reset of the AIMD. This system ensures that no third party can reset an implanted AIMD without the patient being aware of it as long as he/she is awake or conscious. A magnet is rather bulky and inconvenient to constantly carry around and can delete magnetic cards, such as bank cards. Furthermore, it does not allow a secure key/lock system as any magnet could be used to trigger the resetting of the AIMD, thus yielding a limited safety. The magnet action is restricted to resetting the AIMD.

The present invention proposes a solution for reducing the energy consumption associated with the optical triggering of an action by an AIMD from an external triggering unit. It also increases the safety of the system, ensuring that no one can trigger an action without the approval of the patient carrying the AIMD or of a physician. The action can be initiation of a communication between the AIMD and an external communication unit or the triggering of one or more pre-defined actions, such as varying one or more parameters of the electric pulses generated by the IPG, or measuring a physiological sign, such as heart rhythm, oxygen saturation in blood, blood tension, and the like. The present invention can also provide a feedback signal to the user, confirming that the one or more predefined actions have successfully been triggered. Furthermore, the present solution makes it impossible to hack remotely the communication means of the AIMD by sending repeated RF-signals requesting a contact with the implanted communication unit of the AIMD and thus depleting the implanted battery. These and other advantages of the present invention are presented in continuation.

SUMMARY OF THE INVENTION

The present invention is defined in the appended independent claims. Preferred embodiments are defined in the dependent claims. In particular, the present invention concerns a kit-of-parts for initiating an action by an active implantable medical device (AIMD) implanted in a body of a patient triggered by an external triggering unit located outside the body of the patient, the kit-of-parts comprising, (A) the AIMD configured for being implanted in the body of a patient and comprising an encapsulation unit defining an inner volume sealingly separated from an outside of the encapsulation unit by walls, wherein the inner volume comprises an action trigger configured for initiating an action by the AIMD, upon reception of a starting signal from the external triggering unit, wherein the action trigger is electrically coupled to an implanted control logic lodged in the inner volume and configured for controlling operations of the AIMD, (B) the external triggering unit comprising an external emitter configured for emitting the starting signal to the action trigger, wherein, the external emitter comprises one or more sources of light configured for emitting the starting signal in the form of an optical starting signal having a wavelength comprised between 350 and 2200 nm, preferably between 400 and 1500 nm, the walls of the encapsulation unit comprise a transparent wall portion which is transparent to the optical starting signal, and the action trigger is an optical action trigger comprising one or more photodetectors facing the transparent wall portion and configured for transforming the optical starting signal into an electrical signal, which serves to initiate the action by the AIMD.

The action may comprise activating an implanted communication unit lodged in the inner volume, to a state configured for communicating with an external communication unit. For example, the implanted communication unit and the external communication unit can be configured for communicating by one of, an RF-communication preferably in the frequency range between 1 MHz to 2.5 GHz, more preferably a Bluetooth communication or a wifi communication, or an optical communication, preferably in a wavelength range comprised between 350 and 2200 nm, preferably between 400 and 1500 nm.

In one embodiment, the optical action trigger can comprise either a single photodetector or several photodetectors, preferably at least three, more preferably at least four photodetectors arranged in series. With this configuration, the starting signal must activate all the photodetectors in order to generate a voltage equal to or greater than a predefined triggering voltage, required for initiating the action by the AIMD.

In another embodiment, the optical action trigger comprises either a single photodetector, or several photodetectors, preferably at least three, more preferably at least four photodetectors arranged in parallel. With this configuration, the starting signal must activate one or more photodetectors, preferably all the photodetectors, in order to generate a current equal to or greater than a corresponding predefined triggering current, required for initiating the action by the AIMD.

The optical action trigger can be configured for generating a logic signal and for sending the logic signal to the implanted control logic. The logic signal typically depends on the voltage or current generated by the one or more photodetectors. The implanted control logic can be configured for decoding the logic signal and for determining whether or not to initiate the action.

In an embodiment, in order to initiate the action by the AIMD, the starting signal must have a predefined value of one or more parameters selected among a wavelength, an intensity, a frequency, an ON/OFF sequence of predefined number and durations of ON-signals, or a sequence of wavelengths, or a sequence of frequencies.

In a preferred embodiment, the AIMD is a neurostimulator comprising an implanted pulse generator (IPG) lodged in the inner volume and coupled to the implanted control logic, wherein the control logic is configured for controlling operations of the IPG. The IPG comprises a source of energy pulses coupled through an energy conductor to an electrode unit provided with electrodes and configured for being coupled to a tissue of a patient to be electrically stimulated by the electrodes. Preferably, the source of energy pulses is a light source, the energy conductor is an optical fibre, and the electrode unit comprises a photovoltaic cell configured for transforming optical energy propagated through the optical fibre into electrical current to power the electrodes.

For a neurostimulator as defined supra, the action can be one or more of:

establishing a communication between the AIMD and the external communication unit, and modifying one or more parameters of the IPG, including stimulation pulse intensity, pulse frequency, and pulse duration, and/or generating one or more energy pulses or preventing generation of energy pulses.

In a preferred embodiment, the external emitter is configured for sending different types of starting signals. The optical action trigger is configured for transmitting the type of starting signal to the implanted control logic, and the implanted control logic is configured for triggering a predefined corresponding action by the AIMD depending on the type of starting signal received by the optical action trigger. The predefined corresponding action can include one of interrupting stimulation, starting stimulation, or modifying stimulation intensity or duration.

The present invention also concerns a method for initiating an action by an implanted active implantable medical device (AIMD) comprising the following steps,
  providing a kit-of-parts as defined supra, wherein the AIMD is implanted subcutaneously in a patient with the transparent wall portion located towards a skin of the patient,
  sending an optical starting signal with the one or more sources of light of the external triggering unit towards the AIMD,
  allowing the optical action trigger to transform the optical starting signal into an electrical signal and to transmit the electrical signal to the control logic in the form of a logic signal,
  allowing the control logic,
    to assess whether the optical starting signal corresponding to the logic signal allows initiation of an action, and
    if the optical starting signal allows initiation of an action, selecting the action corresponding to the optical signal and controlling the AIMD to implement the action, and
    if the optical starting signal does not allow initiation of an action, ignore the electrical signal.
Wherein the action is selected among establishing a communication between an implanted communication unit housed in the inner volume and an external communication unit located outside the patient's body, and/or measuring a physiological parameter.

BRIEF DESCRIPTION OF THE FIGURES

For a fuller understanding of the nature of the present invention, reference is made to the following detailed description taken in conjunction with the accompanying drawings in which.

DETAILED DESCRIPTION OF THE INVENTION

Figure 1A:
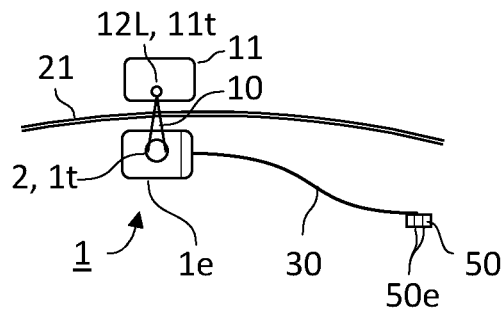
FIG. 1(a): shows an external triggering unit sending a starting signal to a neurostimulator AIMD implanted in a patient body and comprising an encapsulation unit, an electrode unit, and a lead energetically connecting the encapsulation unit to the electrode unit.
Figure 1B:
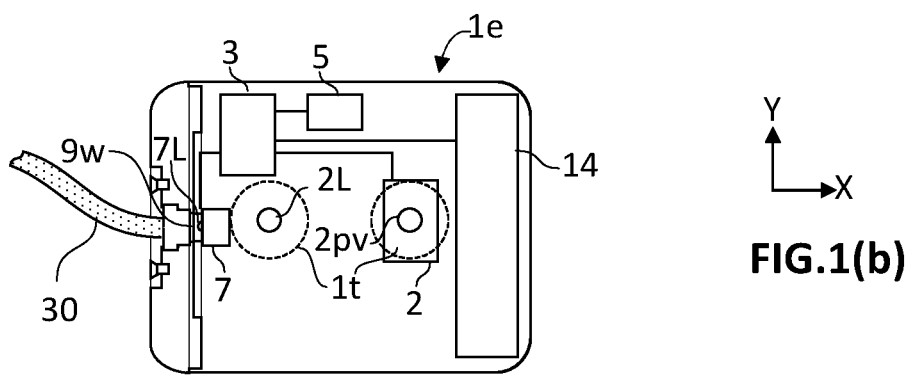
FIG. 1(b): shows an embodiment of neurostimulator AIMD according to the present invention showing some of the components included within the inner volume of the encapsulation unit.

As shown in FIGS. 1(a) and 1(b), the present invention concerns a system including an active implantable medical device (AIMD) (1) configured for being implanted in a patient's body. As shown in FIG. 1(b), the AIMD comprises at least an encapsulation unit (1e) defining an inner volume sealingly separated from an outside of the encapsulation unit by walls (1w). The inner volume comprises an optical action trigger (2) configured for initiating an action by the AIMD (1), upon reception of a starting signal (10) from an external triggering unit (11). The system also comprises the external triggering unit (11) comprising an external emitter (12) configured for emitting the starting signal (10) to the optical action trigger (2). The external emitter (12) comprises one or more sources of light (12L) configured for emitting the starting signal (10) in the form of an optical starting signal having a wavelength comprised between 350 and 2200 nm, preferably between 400 and 1500 nm The optical action trigger (2) comprises one or more photodetectors (2pv) facing a transparent wall portion (1t) of the encapsulation unit (1e) which is transparent to the optical starting signal, and is configured for transforming the optical starting signal into an electrical signal. The AIMD is configured for being implanted with the transparent wall portion (1w) which faces the optical action trigger (2) oriented towards the skin (21) of the patient. The optical action trigger is electrically coupled to an implanted control logic (3) lodged in the inner volume and configured for controlling operations of the AIMD. The electrical signal thus transformed is optionally further treated and is sent to the control logic (3) which assesses whether an action, and optionally which action or sequence of actions can be initiated by the AIMD.

AIMD (1)

The active implantable medical device (AIMD) (1) according to the present invention is configured for being implanted in a patient's body, and is configured for actively interacting with the body it is implanted in, such as by stimulating tissues, monitoring vital signs, and the like. The AIMD of the present invention therefore consumes energy for carrying out these actions and generally comprises a source of power. The source of power can be a battery (14), rechargeable or not, as shown in FIG. 1(b) or can be a coil configured for inducing a current upon exposure to a magnetic field (not shown). In all cases, energy saving is an important issue for implantable devices, affording no easy access to once implanted. The encapsulation unit encloses in the inner volume a control logic (3) which is programmed for controlling the functions of the AIMD. It may enclose an implanted communication unit (5) configured for communicating with an external communication unit (15) located outside the encapsulation unit (1e) and outside the patient's body the AIMD is implanted in.

In its simplest form, the AIMD comprises the encapsulation unit (1e) only. It may emit light pulses to the direct environment thereof. It can also measure physiological signs of the patient, including but not restricted to heart rhythm, oxygen saturation in blood, arterial pressure, temperature, and the like. In a preferred embodiment illustrated in FIG. 1(a), the AIMD is a neurostimulator comprising an implanted pulse generator (IPG) (7) lodged in the inner volume and coupled to the implanted control logic (3), the latter being configured for controlling operations of the IPG. The control logic can be programmed by a physician with a main pulse sequence. The main pulse sequence can also be overruled and replaced by an alternative pulse sequence after the AIMD was implanted by communication between external and implanted communication units (5, 15). The IPG comprises a source of energy pulses coupled through an energy conductor to an electrode unit (50) provided with electrodes (50e) and configured for being coupled to a tissue of a patient to be electrically stimulated by the electrodes. The tissue can be a muscle, a nerve, a brain, or a spinal cord. In one embodiment, the electrode unit (50) is coupled to a vagus nerve of the patient, which is stimulated to treat epilepsy. Instead of electrodes, the electrode unit can comprise optrodes, for irradiating a tissue with an electromagnetic wave, preferably in the visible or IR-wavelength range.

In a preferred embodiment, the source of energy pulses of the IPG (7) is a light source (7L). The energy conductor is an optical fibre (30), and the electrode unit (50) comprises a photovoltaic cell configured for transforming optical energy propagated through the optical fibre (30) into electrical current to power the electrodes (50e). In case of optrodes, the light propagated along the optical fibre is driven directly to the optrodes.

After implantation, an AIMD according to the present invention must also be able to initiate an action upon triggering from the external triggering unit (11). The action can be initiated only upon reception and assessment by the controlling logic of the optical starting signal (10) received by the optical action trigger (2).

The action to be initiated can be activating an implanted communication unit (5) lodged in the inner volume, to a state configured for communicating with an external communication unit (15) located outside the patient's body This way, instructions or stimulation parameters changes can be transmitted from the external communication unit (15) to the implanted communication unit (5), and therefrom to the control logic (3). The action can also include measuring a physiological sign or parameter. The implanted communication unit (5) can transmit information to the external communication unit (15), including but not restricted to physiological parameters measured by sensors of the AIMD, or confirmation of the emission of a pulse or pulse sequence.

Alternatively, or additionally, the action can include modifying one or more parameters of the IPG (7), including but not restricted to a stimulation pulse intensity, a pulse frequency, a pulse duration, generating one or more energy pulses or preventing generation of energy pulses. The implanted communication unit (5) can communicate to the external communication unit (15) whether or not the one or more parameters were modified.

The implanted communication unit (5) and the external communication unit (15) can be configured for communicating by one of, an RF-communication preferably in the frequency range between 1 MHz to 2.5 GHz, more preferably a Bluetooth communication or a WIFI communication, or an optical communication, preferably in a wavelength range comprised between 350 and 2200 nm, preferably between 400 and 1500 nm.

The walls (1w) of the encapsulation unit (1e) comprise a transparent wall portion (1t) transparent to the optical starting signal (10). In a preferred embodiment, the walls of the encapsulation unit are wholly made of a ceramic material transparent to the optical starting signal, such as fused silica, borosilicate, spinel, sapphire, or yttrium oxide material, preferably the single material is fused silica. An example of encapsulation unit made of such ceramic material is described in PCT/EP2019/069087. The optical action trigger (2) must be facing the transparent wall portion (1t) and the latter must face the skin (21) of the patient, to allow the optical action trigger to detect an optical starting signal emitted from the external triggering unit (11), located outside of the patient's body.

The components enclosed within the inner volume of the encapsulation unit, including the optical action trigger, the implanted control logic (3), can be embedded in a transparent resin, such as an epoxy resin, a polyester resin, a polyurethane resin, or the like. The walls (1w) can be made of ceramic as described above, and the inner volume filled with the transparent resin, or the resin can also form the walls (1w) of the encapsulation unit (1e).

The optical action trigger (2) is configured for generating a logic signal and for sending the logic signal to the implanted control logic (3), wherein the logic signal depends on the voltage or current generated by the one or more photodetectors (2pv), and wherein the implanted control logic (3) is configured for decoding the logic signal and for determining whether or not to initiate the action.

External Triggering Unit (11)

Figure 2A:
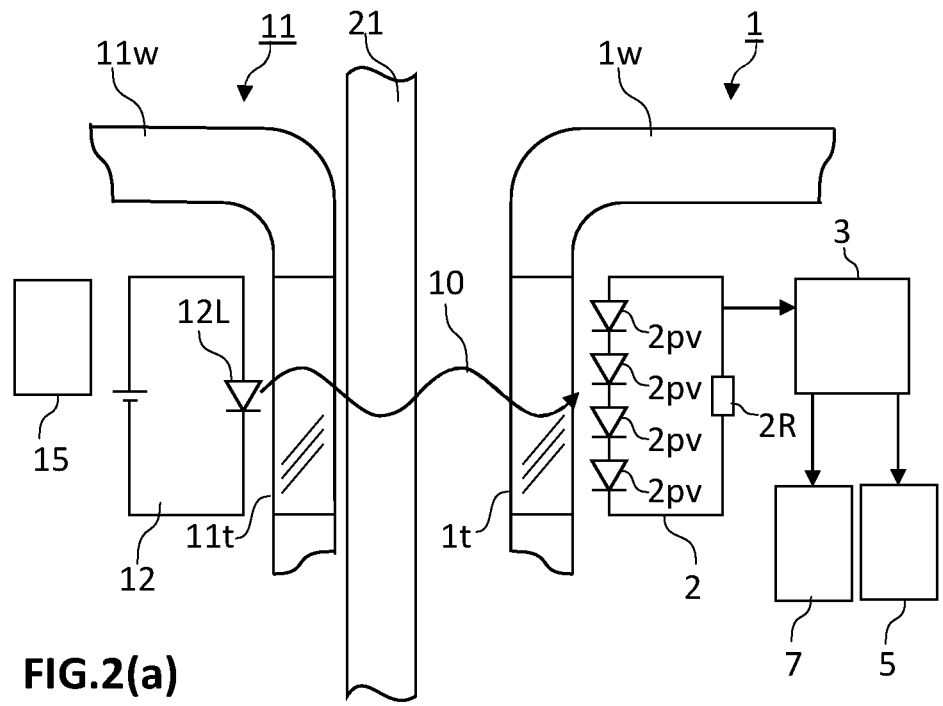
FIG. 2(a): shows a first embodiment of an external triggering unit sending a starting signal to an AIMD according to the invention comprising an optical action trigger coupled to a control logic which controls an implanted communication unit and/or an IPG.
Figure 2B:
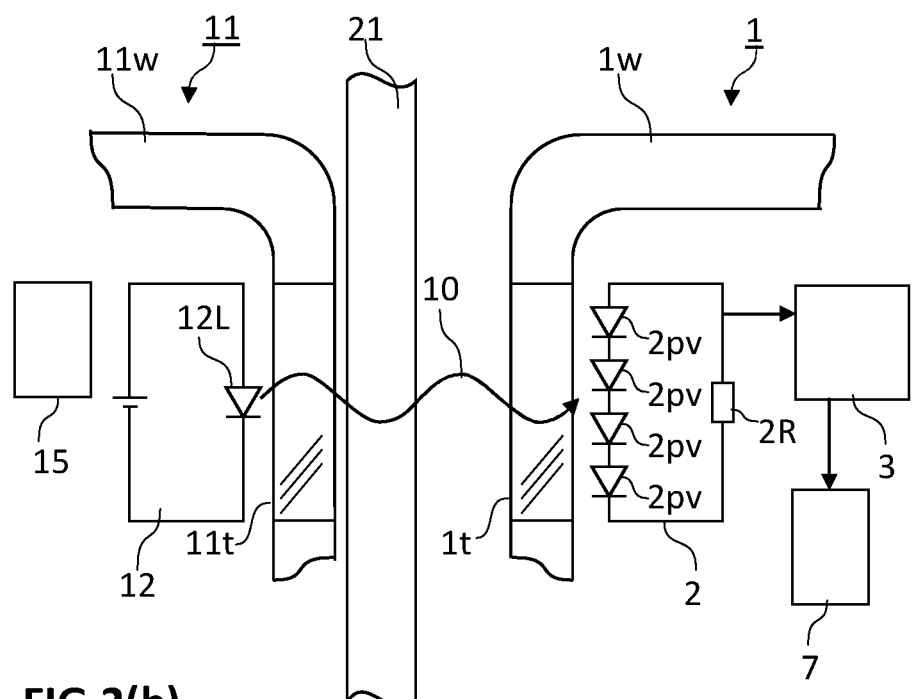
FIG. 2(b): shows a second embodiment of an external triggering unit sending a starting signal to an AIMD according to the invention comprising an optical action trigger coupled to a control logic which controls an IPG.

As illustrated in FIGS. 2(a) and 2(b), the external triggering unit (11) comprises an external emitter (12) configured for emitting the starting signal to the optical action trigger (2). The external emitter (12) comprises one or more sources of light (12L), preferably LED's, configured for emitting the optical starting signal (10) in the form of an optical starting signal (10) having a wavelength comprised between 350 and 2200 nm, preferably between 400 and 1500 nm. The external triggering unit (11) may comprise a housing defined by walls (11w) enclosing the external emitter (12). The housing must comprise at least a transparent wall portion (11t) which is transparent to the optical starting signal (10) and facing the one or more sources of light (12L).

In its simplest form, the external triggering unit comprises the external emitter (12) only. In a preferred embodiment, the external triggering unit also comprises a control logic and/or a memory storing one or more predefined optical starting signals characterized by corresponding predefined values of one or more optical starting signal parameters (P) selected from one or more of a wavelength, an intensity, a frequency, an ON/OFF sequence of predefined number and durations of ON signals, or a sequence of wavelengths, or a sequence of frequencies, and the like. In yet a preferred embodiment, alternative or concomitant with the foregoing embodiment, the external triggering unit comprises the external communication unit (15).

Figure 3A:
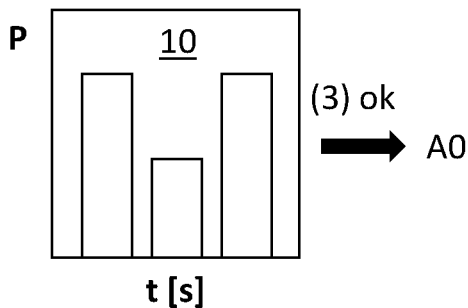
FIG. 3(a): shows a starting signal characterized by a parameter (P) assessed as allowable by the control logic, thus allowing triggering of an action A0.
Figure 3B:
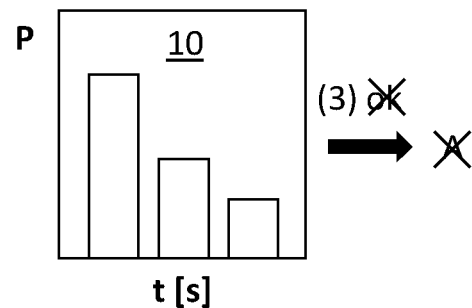
FIG. 3(b): shows a starting signal characterized by a parameter (P) assessed as not allowable by the control logic, thus preventing triggering of any action A.
Figure 3C:
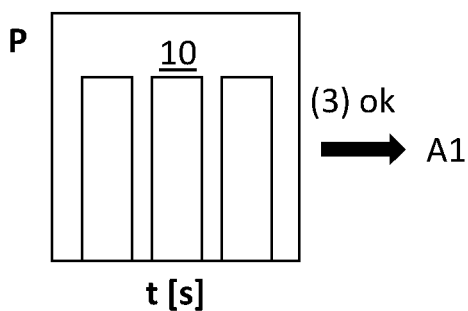
FIG. 3(c): shows a starting signal characterized by a parameter (P) assessed as allowable by the control logic, corresponding to a specific action A1 different from action A0, which is then triggered.

FIGS. 3(a) to 3(c) illustrate examples of optical starting signals having a parameter (P) varying with time. In one embodiment, the predefined value of the one or more optical starting signal parameters defines a key, which must fit a lock to trigger the action. For example, FIG. 3(a) illustrates a first optical starting signal characterized by a parameter (P) changing according to a first time sequence. When initiation of an action is desired, the first optical starting signal (10) is emitted towards the optical action trigger (2), thus generating a voltage and a first logic signal, which is analysed by the control logic (3). If the first logic signal corresponding to the first optical starting signal (10) is identified as valid, a first action (A0) can be initiated. If, as illustrated in FIG. 3(b), the control logic (3) does not recognize a second logic signal corresponding to a second optical starting signal as being valid, no action (A) is initiated. The external triggering unit (11) can have a user interface allowing the user (the patient or a physician) to select which action is to be initiated by the AIMD. The user interface can be a series of keys or push buttons, or can include a screen, preferably a touch screen.

Figure 3D:
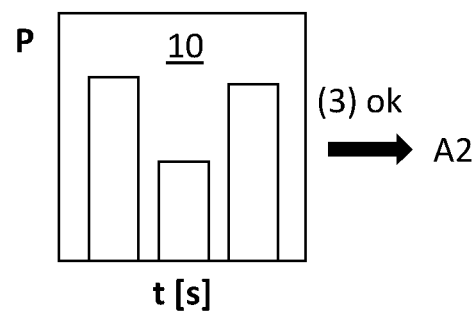
FIG. 3(d): shows a starting signal characterized by a parameter (P) assessed as allowable by the control logic, corresponding to a specific action A2 different from actions A0 and A1, which is then triggered.

The control logic (3) can store several logic signals corresponding to specific optical starting signals (10) each characterized by a different time sequence, and each associated to a different action (A0, A1, A2), This is illustrated in FIGS. 3(a), 3(c), and 3(d), each showing a first, second, and third time sequences, each recognized by the control logic as valid, and each initiating a different action (A0, A1, A2), which is predefined in the control logic. In this embodiment, the external emitter (12) is configured for sending different types of optical starting signals (10). The optical action trigger (2) is configured for generating corresponding logic signals and transmitting the logic signals to the implanted control logic (3). The implanted control logic (3) is configured for triggering a predefined corresponding action by the AIMD depending on the type of logic signal corresponding to the optical starting signal received by the optical action trigger. The corresponding action can include initiating a communication between the implanted communication unit (5) and the external communication unit (15). In case of neurostimulators, the predefined corresponding action can include one of interrupting stimulation, starting stimulation, or modifying initial stimulation parameters, including stimulation intensity frequency, shape, and the like, for a given time, after which a return to a stimulation with the initial stimulation parameters is programmed. A corresponding action can be measuring a physiological sign of the patient. Preferably, the action also includes establishing a communication between the implanted communication unit (5) and the external communication unit (15) to transfer a result of the physiological sign thus measured.

Alternatively, a single starting signal can be emitted by the external emitter (12) to initiate a communication between the implanted communication unit (5) and the external communication (15), which start with an exchange of encrypted signals which are verified by the control logic (3). Once approved, communication can start with transfer of information including which action or sequence of actions is to be activated by the AIMD.

The one or more light sources (12L) preferably comprise LED's. Because the one or more sources of light (12L) can be very small, and so can a control logic or memory, the external triggering unit (11) can be very small in volume. The external triggering unit (11) is preferably wearable by the patient, preferably mounted on a bracelet, on a watch, or a necklace, a smart phone, or the like, to be worn at a wrist, a neck, a belt, a pocket, and the like. As shown in FIGS. 1(a), and 2(a), 2(b), the optical starting signal (10) must propagate through the skin (21) and tissues separating the transparent wall portion (1t) of the AIMD from the skin (21) of the patient.

Optical Action Trigger (2)

As illustrated in FIGS. 2(a) and 2(b), the optical action trigger (2) is enclosed in the inner volume of the encapsulation unit (1e) and comprises one or more photodetectors (2pv) facing the transparent wall portion (1t) and configured for transforming the optical starting signal (10) into an electrical signal, which serves to initiate the action by the AIMD.

The optical action trigger can comprise either a single photodetector (2pv), or several photodetectors, preferably at least three, more preferably at least four photodetectors. In a first embodiment the several photodetectors are arranged in series. It is preferred that the optical starting signal (10) must activate all the photodetectors in order to generate a voltage equal to or greater than a predefined triggering voltage, required for initiating the action by the AIMD. If the predefined triggering voltage is not reached, the control logic (3) is not even informed that an optical starting signal (10) had been sent, and no action can be initiated.

Figure 4A:
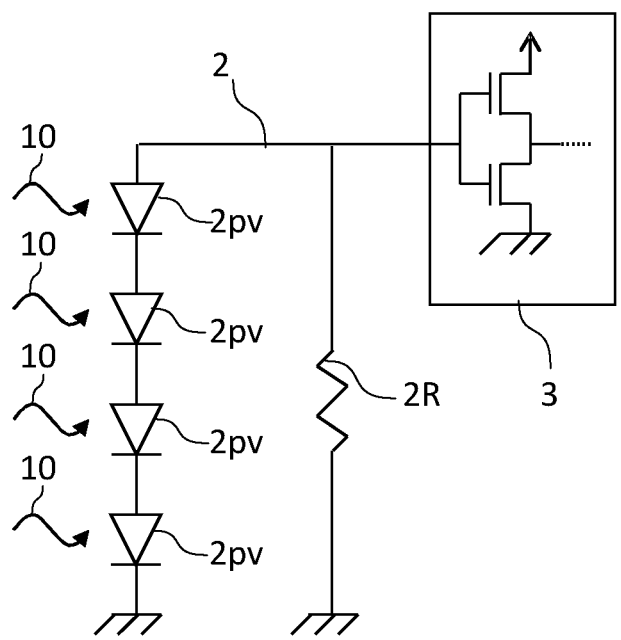
FIG. 4(a): shows a circuit comprising several photodetectors arranged in series and resistors with an input of a classical CMOS inverter.

In an alternative embodiment, the several photodetectors are arranged in parallel, and the optical starting signal (10) must activate one or more photodetectors, preferably all the photodetectors, in order to generate a current equal to or greater than a corresponding predefined triggering current, required for initiating the action by the AIMD. Again, if the predefined triggering current is not reached, the control logic (3) is not even informed that an optical starting signal (10) had been sent, and no action can be initiated Upon receiving optical power, the several photodetectors generate an electrical current. An electrical circuit is required to convert this electrical current into a usable logic signal for the control logic (3). One embodiment is the circuit of FIGS. 2(a), 2(b), and 4(a), comprising several photodetectors (2pv) arranged in series and a resistor (2R). The current generated by the several photodetectors flows through the resistor (2R) of a chosen value (e.g., 100 kΩ), thus generating a voltage at the resistor and at an input of the control logic (3). The input can be, as illustrated in FIG. 4(a) for example, a classical CMOS inverter. Such inputs typically consume no input current and have no static consumption.

When, upon detection of an optical starting signal, the voltage level rises above a predefined triggering voltage, a logic transition occurs wherein the logic signal passes for example from 0 to 1, and triggers the control logic (3) to check the optical starting signal. The thus generated logic signal can be transferred to the control logic (3) as an analog or digital signal for assessment. In its simplest form, the optical starting signal (10) can be a simple light pulse, causing the voltage in the optical action trigger to rise along a rising slope to a given value. If the voltage value thus reached is sufficient, a logic signal is generated and sent to the control logic (3) for initiating a given action. In a more sophisticated embodiment illustrated in FIGS. 3(a) to 3(d), the optical starting signal (10) formed by a single pulse or by a sequence of pulses is characterized by specific values of one or more parameters (P). In one embodiment, a logic signal is formed and sent to the control logic (3) only in case the values of the optical starting signal (10) fulfils the required values of the one or more parameters. This increases substantially the safety of the system by imposing a key to initiate an action. In yet a preferred embodiment, a given set of values of one or more parameters of the single pulse or of the sequence of pulses is associated to a specific action to be initiated.

The number of photodetectors and technology is chosen so that the resulting voltage level is sufficient for generating a logic transition e.g., from 0 to 1 in case of a digital logic signal. The value of the resistor (2R) is chosen to fulfil antagonistic requirements of high voltage and a swift discharge of the capacitance. This requires a compromise: between a resistor value as high as possible so that little current is needed to reach the predefined triggering voltage; and a value sufficiently low so that when the optical power disappears, the capacitive discharge of the capacitance of the input of the control logic through the resistor is sufficiently fast to allow for modulated signal at high frequency. Note that a resistor value which is too high could in certain conditions also render the circuit too sensitive to capture noise.

Figure 4B:
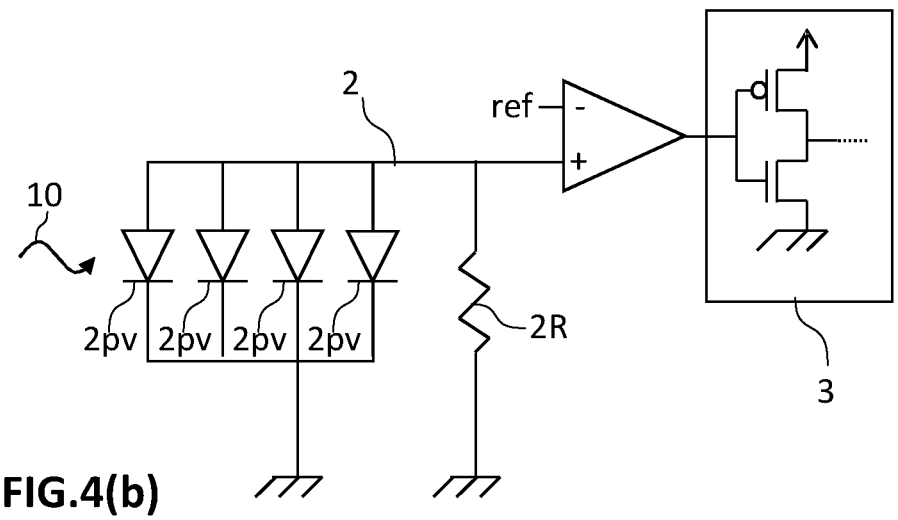
FIG. 4(b): shows a circuit comprising several photodetectors arranged in parallel and resistors.

In an alternative embodiment illustrated in FIG. 4(b), the circuit comprises several photodetectors (2pv) arranged in parallel and a resistor (2R). With this configuration, the voltage level is usually not sufficient for a classical logic transition and an intermediate voltage comparator—which consumes somehow—compares the generated voltage against a reference voltage and outputs a corresponding voltage level in line with logic levels needed by the control logic (3).

A main advantage of the present invention is that the optical action trigger consumes no power at all until it receives an optical starting signal (10). Since the starting signal is an optical starting signal which must propagate through skin (21) and tissues located between the implanted AIMD and the external triggering unit (11), close proximity is needed and therefore no hacking of the AIMD system or malevolent wearing of the battery power is possible without the patient knowing about it. Indeed, the external triggering unit (11) must be held close to, even in contact with the skin (21) of the patient to ensure that the optical starting signal (10) reaches the optical action trigger (2) of the AIMD with sufficient intensity to allow the initiation of the desired action. The optical action trigger is magnet free, which is advantageous for being MRI compatible, with no risk of deletion of magnetic cards (e.g., bank cards), and the like. It also combines high velocity and low to no power consumption, when in corresponding electrical systems power consumption generally increases with the velocity of the system.

Control Logic (3) and Action Initiation

Once an optical starting signal (10) is received by the optical action trigger (2), it is transferred to the control logic (3) as a digital signal for assessment. For example, as illustrated in FIGS. 2(a) and 2(b), the current generated by the one or more photodetectors (2pv) loads a resistor (2R), providing an increase of voltage, and subsequent decrease, which generates a logic pulse. A first stage of the assessment process is the assessment of whether the optical starting signal (10) received by the optical action trigger (2) allows the initiation of an action. The control logic (3) compares the signal received with a library of patterns stored in an implanted memory. If a match between the optical starting signal and the pattern stored in the memory occurs, then the control logic can start a second stage of the assessment.

If the action corresponding to the optical starting signal (10) is establishing a communication between an implanted communication unit (5) and an external communication unit (15), then a second stage of the assessment process consists of initiating said communication. The external communication unit (15) can be part of the external triggering unit (11). In order to keep the dimensions of the external triggering unit (11) as small as possible, however, the external communication unit (15) can instead be separate from the external triggering unit (11). An action can also be a measurement of a physiological parameter. A second stage can therefore include carrying out such measurement. For neurostimulators comprising an IPG (7), the action corresponding to the optical starting signal (10) can be any one of generating one or more energy pulses, preventing generation of energy pulses, or modifying a stimulation parameter including pulse intensity or pulse duration, or pulse frequency, and the like. In this case, a second stage of the assessment process is to control the IPG accordingly. The action can be a sequence of actions. For example, a sequence of action could be the IPG (7) to generate a particular pulse followed by the implanted communication unit (5) to send to the external communication unit (15) a confirmation of the generation of the pulse or a value of a physiological sign measured following the generation of the pulse. FIG. 2(a) shows the control logic (3) coupled to the optical action trigger (2) for receiving the signal therefrom, and upon assessment of the signal, the control logic can control the implanted communication unit (5) and/or the IPG (7). In the embodiment of FIG. 2(b), the action concerns controlling the IPG (7).

If the control logic (3) stores several types of actions, a second stage of the assessment process is to select the action or actions sequence corresponding to the particular optical starting signal (10) received by the optical action trigger (2). A third stage of the assessment process is then to control either the implanted communication unit (5), a sensor for measuring a physiological parameter, or the IPG (7) accordingly, or to implement any other action or sequence of actions.

Method for Initiating an Action by an Implanted Aimd

The system or kit-of-parts of the present invention is suitable for use in a method for initiating an action by an implanted AIMD. The method comprises the following steps, providing an AIMD (1) and an external triggering unit (11) as defined supra, sending an optical starting signal (10) with the source of light (12L) of the external triggering unit (11) towards the AIMD implanted subcutaneously in a patient with the transparent wall portion (1t) located towards the skin (21) of the patient, allowing the optical action trigger (2) to transform the optical starting signal into an electrical signal and to transmit the electrical signal to the control logic (3) in the form of a logic signal, allowing the control logic (3),
  to assess whether the optical starting signal (10) corresponding to the logic signal allows initiation of an action, and
  if the optical starting signal (10) allows initiation of an action, selecting the action corresponding to the optical signal (10) and controlling the AIMD to implement the action, and
  if the optical starting signal (10) does not allow initiation of an action, ignore the electrical signal.

The action can be anyone of, establishing a communication between an implanted communication unit (5) housed in the inner volume and an external communication unit (15) located outside the patient's body, measuring a physiological parameter, such as heart rhythm, vascular tension, oxygen saturation in blood, and the like, modifying one or more parameters of the IPG, including one of interrupting stimulation, starting stimulation, or modifying stimulation intensity, duration, or any other parameter of the stimulation.

The action can also be a sequence of two or more of the foregoing actions, or include any other action such as resetting the AIMD, or changing the stimulation programming.

One main advantage of using an optical action trigger (2) together with a source of light (12L) mounted on an external triggering unit (11) to initiate an action by the AIMD is that the optical action trigger (2) is idle and does not consume any power as long as the one or more photodetectors (2pv) do not receive an optical starting signal (10). In a preferred embodiment, once an optical starting signal (10) has been sent, the optical action trigger (2) and control logic (3) can be powered by the one or more sources of light (12L) of the external triggering unit (11) throughout the process of assessment of the optical starting signal, by simply letting the source of light (12L) on to irradiate the one or more photodetectors (2pv) which generate an electrical current. In a most preferred embodiment, the one or more sources of light (12L) can also be used to provide the required power to carry out the required action. This is advantageous in that it spares the implanted battery (14). It has the drawback that the external triggering unit (11) must be maintained in position on the skin (21) of the patient during the whole duration required for carrying out the action.

| REF | DESCRIPTION |
| --- | --- |
| 1 | AIMD |
| 1e | Encapsulating unit |
| 1t | Transparent wall portion of encapsulation unit |
| 1w | Wall of encapsulation unit |
| 2 | Optical action trigger |
| 2pv | Optical action trigger photovoltaic cell |
| 2R | Optical action trigger resistance |
| 3 | Control logic |
| 5 | Implanted communication unit |
| 7 | Implantable Pulse Generator (IPG) |
| 7L | IPG light source |
| 9w | Window facing IPG light source |
| 10 | Starting signal |
| 11 | External triggering unit |
| 11t | Transparent wall portion of external triggering unit |
| 12 | External light circuit |
| 12L | External light source |
| 14 | Battery |
| 15 | External communication unit |
| 21 | Skin |
| 30 | Optical fibre |
| 50 | Electrode unit |
| 50e | Electrode |
| A | Predefined action |
| A0-A2 | Specific predefined actions |

The invention claimed is:

1. A kit of parts for initiating an action by an active implantable medical device (AIMD) (1) implanted in a body of a patient triggered by an external triggering unit (11) located outside the body of the patient, the kit-of-parts comprising,
(A) the AIMD (1) configured for being implanted in the body of a patient and comprising an encapsulation unit (1e) defining an inner volume sealingly separated from an outside of the encapsulation unit by walls (1w), wherein the inner volume comprises an action trigger configured for initiating an action by the AIMD (1), upon reception of a starting signal (10) from the external triggering unit (11), wherein the action trigger is electrically coupled to an implanted control logic (3) lodged in the inner volume and configured for controlling operations of the AIMD,
(B) the external triggering unit (11) comprising an external emitter (12) configured for emitting the starting signal to the action trigger,
wherein
the external emitter (12) comprises one or more sources of light (12L) configured for emitting the starting signal (10) in the form of an optical starting signal having a wavelength between 350 and 2200 nm,
the walls of the encapsulation unit comprise a transparent wall portion (1t) which is transparent to the optical starting signal, and
the action trigger is an optical action trigger (2) comprising one or more photodetectors (2pv) facing the transparent wall portion (1t) and configured for transforming the optical starting signal (10) into an electrical signal, which serves to initiate the action by the AIMD
characterized in that, the optical action trigger (2) is idle and does not consume any power as long as the one or more photodetectors (2pv) do not receive an optical starting signal (10).

2. The kit of parts according to claim 1, wherein the action comprises activating an implanted communication unit (5) lodged in the inner volume, to a state configured for communicating with an external communication unit (15).

3. The kit of parts according to claim 2, wherein the implanted communication unit (5) and the external communication unit (15) are configured for communicating by one of,
an RF-communication in the frequency range between 1 MHz to 2.5 GHz, or
an optical communication, in a wavelength range between 350 and 2200 nm.

4. The kit of parts according to claim 1, wherein the optical action trigger comprises either a single photodetector (2pv) or at least three arranged in series, and wherein the starting signal (10) must activate all the photodetectors in order to generate a voltage equal to or greater than a predefined triggering voltage, required for initiating the action by the AIMD.

5. The kit of parts according to claim 1, wherein the optical action trigger comprises either a single photodetector (2pv) or several photodetectors, preferably at least three arranged in parallel, and wherein the starting signal (10) must activate one or more photodetectors, preferably all the photodetectors, in order to generate a current equal to or greater than a corresponding predefined triggering current, required for initiating the action by the AIMD.

6. The kit of parts according to claim 4, wherein the optical action trigger (2) is configured for generating a logic signal and for sending the logic signal to the implanted control logic (3), wherein the logic signal depends on the voltage or current generated by the one or more photodetectors (2pv), and wherein the implanted control logic (3) is configured for decoding the logic signal and for determining whether or not to initiate the action.

7. The kit of parts according to claim 1, wherein in order to initiate the action by the AIMD, the starting signal (10) must have a predefined value of one or more parameters selected among a wavelength, an intensity, a frequency, an ON/OFF sequence of predefined number and durations of ON-signals, or a sequence of wavelengths, or a sequence of frequencies.

8. The kit of parts according to claim 1, wherein,
the AIMD is a neurostimulator comprising an implanted pulse generator (IPG) (7) lodged in the inner volume and coupled to the implanted control logic (3), wherein the control logic is configured for controlling operations of the IPG, the IPG comprises a source of energy pulses coupled through an energy conductor to an electrode unit (50) provided with electrodes (50e) and configured for being coupled to a tissue of a patient to be electrically stimulated by the electrodes.

9. The kit of parts according to claim 8, wherein the source of energy pulses is a light source (7L), the energy conductor is an optical fibre (10), and the electrode unit (50) comprises a photovoltaic cell configured for transforming optical energy propagated through the optical fibre (30) into electrical current to power the electrodes (50e).

10. The kit of parts according to the claim 8, wherein the action is selected between one or more of:

establishing a communication between the AIMD (1) and the external communication unit (15), and modifying one or more parameters of the IPG (7), including stimulation pulse intensity, pulse frequency, and pulse duration, and/or generating one or more energy pulses or preventing generation of energy pulses.

11. The kit of parts according to claim 10, wherein the action comprises modifying the one or more parameters of the IPG (7), and communicating to an external communication unit (15) whether or not the one or more parameters were modified.

12. The kit of parts according to claim 1, wherein the external emitter (12) is configured for sending different types of starting signals (10), the optical action trigger (2) is configured for transmitting the type of starting signal to the implanted control logic, and wherein the implanted control logic (3) is configured for triggering a predefined corresponding action by the AIMD depending on the type of starting signal received by the optical action trigger (2).

13. The kit of parts according to claim 12, wherein the predefined corresponding action includes one of interrupting stimulation, starting stimulation, or modifying stimulation intensity or duration.

14. A method for initiating an action by an implanted active implantable medical device (AIMD) (1) comprising the following steps, providing a kit-of-parts according to claim 1, sending an optical starting signal (10) with the one or more sources of light (12L) of the external triggering unit (11) towards the AIMD, allowing the optical action trigger (2) to transform the optical starting signal (10) into an electrical signal and to transmit the electrical signal to the control logic (3) in the form of a logic signal, allowing the control logic (3), to assess whether the optical starting signal (10) corresponding to the logic signal allows initiation of an action, and if the optical starting signal (10) allows initiation of an action, selecting the action corresponding to the optical signal (10) and controlling the AIMD to implement the action, and if the optical starting signal (10) does not allow initiation of an action, ignore the electrical signal, and wherein the action is selected among establishing a communication between an implanted communication unit (5) housed in the inner volume and an external communication unit (15) located outside the patient's body, and/or measuring a physiological parameter.

* * * * *